United States Patent [19]

Katsunuma

[11] 4,229,571

[45] Oct. 21, 1980

[54] GLUCOCORTICOID SPARING FACTOR AND PROCESS FOR THE PRODUCTION OF THE SAME

[76] Inventor: Nobuhiko Katsunuma, No. 1-78, Shōmachi, Tokushima-shi, Tokushima-ken, Japan

[21] Appl. No.: 933,083

[22] Filed: Aug. 10, 1978

[30] Foreign Application Priority Data

Aug. 16, 1977 [JP] Japan ............................ 52-98110

[51] Int. Cl.² .................................... A61K 31/70
[52] U.S. Cl. ................................ 536/18; 424/115; 435/72; 435/170; 435/873

[58] Field of Search ................... 424/115, 116, 181; 195/96; 435/72, 170, 873; 536/18

[56] References Cited

U.S. PATENT DOCUMENTS 3,928,568  12/1975  Katunuma ..................... 424/115

Primary Examiner—Robert J. Warden
Attorney, Agent, or Firm—Browdy and Neimark

[57] ABSTRACT

A glucocorticoid sparing factor (GSF) which amplifies to liver enzyme induction which is caused in glucocorticoid and a process for the production of GSF are disclosed. GSF can be isolated from the culture broth of a microorganism of the Family Enterobacteriaceae.

8 Claims, 2 Drawing Figures

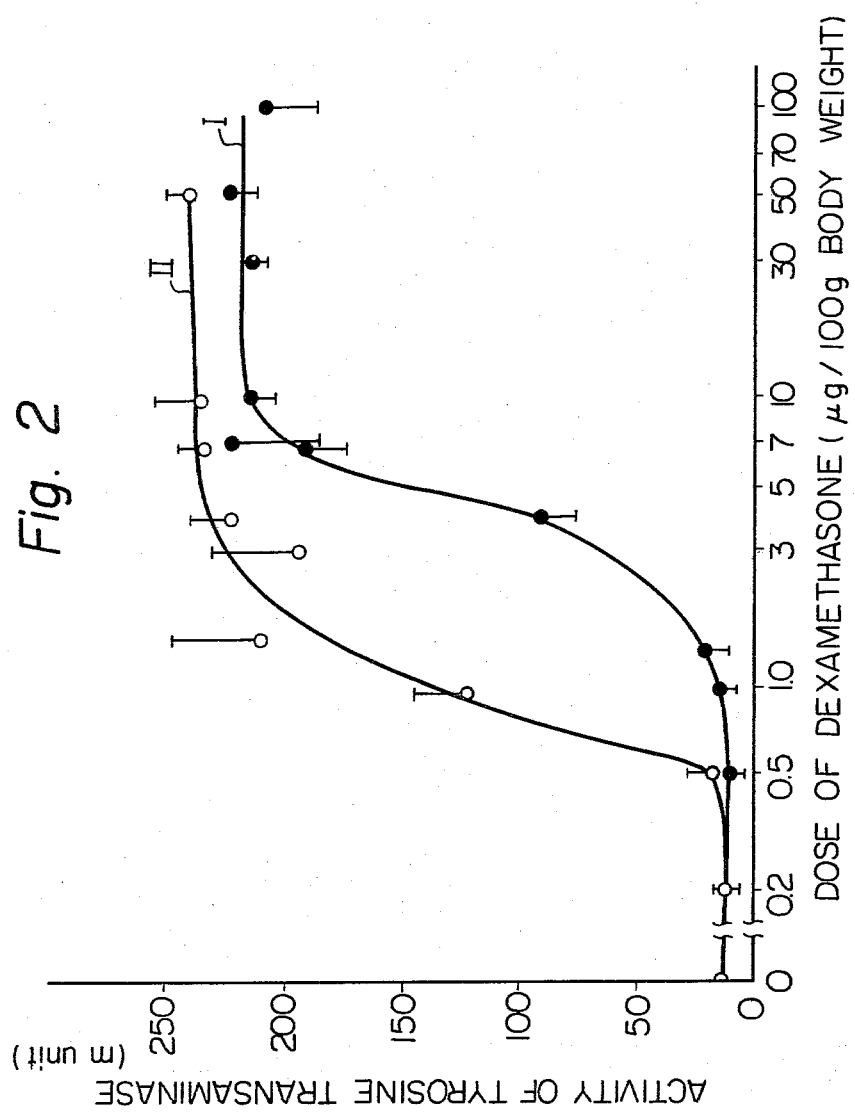

GLUCOCORTICOID SPARING FACTOR AND PROCESS FOR THE PRODUCTION OF THE SAME

This invention relates to a substance amplifying the activities of glucocorticoid and a process for the production of said substance.

The inventor of this invention succeeded in isolating a peptide which amplifies the induction of tyrosine transaminase, as a product from a microorganism of the Family Enterobacteriaceae, such as *Proteus mirabilis*. Thereafter, the inventor continued his study on the influence of metabolic substances from *Proteus mirabilis* upon the various enzymes, and found a novel oligosaccharide which amplifies liver enzyme induction which is caused by glucocorticoid in the metabolic product. The oligosaccharide is referred to as glucocorticoid sparing factor of GSF hereunder.

Thus, this invention relates to GSF and to a process for the production of the same.

In accordance with this invention, GSF is produced by a process which comprises cultivating a microorganism of the Family Enterobacteriaceae under the conventional cultivating conditions, recovering bacterial cells by centrifugation or filtration, extracting bacterial substances, for example, by sonic destruction of the cells and, after deprotenization, treating the extract with activated charcoal. The object substance adsorbed on the surface of activated charcoal is then eluted with proper liquid such as alkali-acetone mixture or a 10–30% aqueous ethanol and purified by appropriate purification such as gel filtration or column chromatography on an ion exchanger to obtain a purified object substance. The substance may be lyophilized for long term storage. The microorganism of the Family Enterobacteraceae which are employed according to this invention are those microorganisms belonging to the genera of Escherichia, Aerobacter, Klebsiella, Paracolobactrum, Alginobacter, Erwinia, Serratia, Salmonella, Proteus and Shigella. Examples of the species include *Escherichia coli, Erwinia aroidaae, Erwinia carotovora, Serratia marcescens, Proteus mirabilis, Proteus vulgaris, Proteus morganii, Aerobacter aerogenes* and the like. All of them are well-known and easily available microorganisms of the Family Enterobacteraceae.

The filter mediums which are useful in the gel filtration in accordance with this invention include, for example, Sephadex G and Sephadex LH-20 (manufactured by Pharmacia Fine Chemicals AB, Sweden) and Polystyrene gel G 3000S (manufactured by Toyo Soda Kabushiki Kaisha, Japan). The ion exchangers which are useful for the column chromatography of this invention include, for example, ion exchange celluloses such as diethylaminoethyl (DEAE) cellulose or ion exchange resins such as Dowex type ion exchange resin.

The thus obtained GSF is a substance having the following physical and chemical properties:
  a. Colorless and acidic;
  b. Easily soluble in water and in a diluted aqueous acid or alkali;
  c. Positive to 1,10-phenanthroline reaction, Orcinol reaction and Anthrone reaction; Negative to Folin-Thiocalt reaction and Elson-Morgan reaction;
  d. Ultraviolet absorption spectrum being as shown in FIG. 1 wherein a gentle shoulder is seen at 265 nm; but, after purification in a manner as in Example 2 below, a sharp peak appears at the same wavelength;
  e. Molecular weight being presumed to be between about 800 to 1,500, calculated from the elution curve obtained with the use of Sephadex G-25 (manufactured by Pharmacia Fine Chemicals AB, Sweden);
  f. Rf being about 0.16 as measured by ascending method using filter paper, preferably, Toyo filter paper No. 526 (Toyo Roshi Kabushiki Kaisha, Japan) and acetic acid-n-butanol-water (3:12:5 v/v) as a developing agent; and
  g. Having N-acetylneuraminic acid, pentose, hexose and a primary amine as constructing moieties.

Aside from the above physical and chemical properties, GSF has the following biological properties:

1. GSF indicates in vivo an amplifying action on the induction of tyrosine transaminase and leucine transaminase by glucocorticoid (triamcinolone or dexamethasone) in liver of adrenalectomized rat.

2. In case an adrenalectomized rat is administered with GSF alone, the induction of liver tyrosine transaminase is not influenced by the administration.

3. GSF does not influence the induction of liver tyrosine transaminase of rat by glucagon or insulin.

4. GSF indicates an amplifying action on the induction of the tyrosine transaminase by glucocorticoid in in vitro system using liver of adrenalectomized rat under the perfusion method, when GSF is added to the system prior to or at the same time as the administration of glucocorticoid.

5. The addition of GSF indicates an amplifying action on the induction of tyrosine transaminase in a tissue-culture of liver cancer cells 7288.

6. If GSF receives the action of $\alpha$-glucosidase, all of the biological activities enumerated above are lost. In contrast, the activities of GSF are not affected at all by the action of any one of $\alpha$-amylase, neuraminidase, hyaluronidase, lysozyme, chymotripsin, trypsin, pepsin, proteinase, papain, collagenase, aminopeptidase M, carboxypeptidase A and B, leucine-aminopeptidase, deoxyribonuclease 1, ribonuclease $T_1 + A$, acid phosphatase and alkali phosphatase.

7. GSF is completely deactivated to form reducing sugar if it is heated in a 6 N hydrochloric acid at 105° C. for 12 hours. While, it is not deactivated for 48 hours in a buffer solution having a pH of 4.2–9 at 37° C.

As mentioned above, GSF according to this invention has a strong amplifying action on enzyme induction caused by glucocorticoid, and, therefore, it is useful for treatment of various diseases which have been objects for medication of glucocorticoid, such as lymphatic leukemia, diffuse collagen disease or infectious disease.

FIG. 2 is a graph illustrating the activities of GSF according to this invention.

Figure 1:
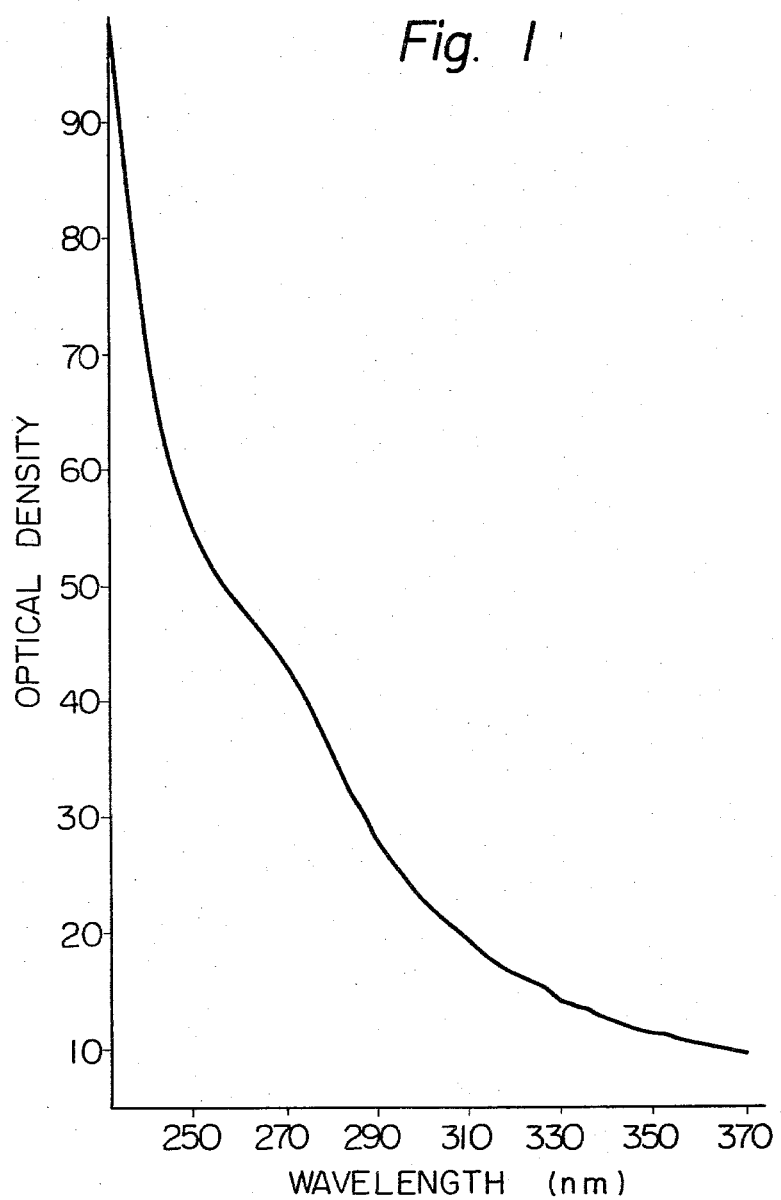
FIG. 1 is a chart of ultraviolet light absorption spectrum of GSF according to this invention. In the chart, vertical axis shows optical density and horizontal axis shows the wavelength.

This invention is further illustrated by the following Examples and Experiments.

EXAMPLE 1

The microorganism, *Proteus mirabilis* (ATCC 21718) was mass-cultivated in Stephenson-Whethem medium and the propagated cells were recovered by filtration and washed with a 0.9% sodium chloride aqueous solution. The cells (18 kg) were suspended in a 2.8% perchloric acid aqueous solution (54 l.), and sonicated with Kubota Model 200$\mu$ sonic generator at 180 W for 7 minutes. After the addition of a 2.8% perchloric acid aqueous solution in an amount twice the volume of the sonicated liquid, the mixture was centrifuged at 8,500 G for 20 minutes, and to the supernatant was added activated charcoal in an amount corresponding to 5 g/l. while stirring. The activated charcoal was recovered by filtration, washed five times with 2 l. of 2.8% perchloric acid aqueous solution and dried. To the dried charcoal was added 700 ml. of 0.2 N aqueous potassium hydroxide-acetone (3:7, v/v) followed by stirring for 30 minutes. The mixture was neutralized by addition of a 10% perchloric acid aqueous solution and filtered. The filtrate was concentrated at 37° C. under reduced pressure and the resulting precipitates were removed from the concentrate by filtration. The concentrate was then passed through a column (6.0 cm in diameter×25 cm long) filled with Sephadex G-10 (manufactured by Pharmacia Fine Chemicals AB, Sweden) to be desalted. The eluate was passed through a column (6.0 cm in diameter×12 cm long) filled with Dowex 50 W (H+type) (manufactured by The Dow Chemical Company, U.S.A.) which had been equilibrated with water, and then the column was washed with distilled water until the eluate did not indicate an absorption at 260 nm.

The column was eluted with 1.5 l. of a 1 N ammonium hydroxide aqueous solution and the eluate was lyophilized. The lyophilized product was dissolved in a very small amount of a 0.01 M potassium phosphate buffer solution (pH, 7.7) and the solution was passed through a column (4.1 cm in diameter×4.5 cm long) filled with DEAE-cellulose and eluted with the same buffer solution until the eluate indicated an absorption less than 0.1 at 260 nm. The eluate was again lyophilized.

The product was again chromatographed on Sephadex G-25 with a column of 3.2 cm in diameter and 63 cm long and eluted with distilled water at a rate of 65 ml./hour and collected as fractions of 4.2 ml. each. Since the active substance was eluted in the fractions No. 89 to 103, they were combined and concentrated by lyophilization.

The concentrate was chromatographed with Toyo Filter paper No. 526 (Toyo Roshi Kabushiki Kaisha, Japan) using acetic acid-n-butanol-water (3:12:5, v/v) as a developing agent by an ascending method to give a spot of object substance (Rf:0.16) between the two fluorescent spots (Rf:0.05 and Rf:0.25).

The spot of Rf:0.16 was extracted with water and evaporated to give the purified object substance.

The degree of purity of the substance and the extent of amplification of the action of glucocorticoid were determined after each of the purification steps mentioned above and compared to values obtained after the purification step with Dowex-50 W (H+type).

The results are shown in the Table 1 below.

TABLE 1

| Operation Step | Total Volume of liquid (ml) | Hexose Content (mg) | Total Activities (units) | Specific Activities (units /g) | Degree of Purity (times) | Yield (%) |
| --- | --- | --- | --- | --- | --- | --- |
| Dowex-50W (H+ type) | 1500 | 343.5 | 11250 | 32.8 | 1 | 100 |
| DEAE-cellulose | 830 | 30.4 | 5561 | 176.3 | 5.4 | 49.4 |
| Sephadex G-25 | 220 | 11.9 | 4608 | 387.2 | 11.8 | 41.0 |
| Paper- | 15 | 0.6 | 1686 | 2810.0 | 85.7 | 14.3 |

TABLE 1-continued

| Operation Step | Total Volume of liquid (ml) | Hexose Content (mg) | Total Activities (units) | Specific Activities (units /g) | Degree of Purity (times) | Yield (%) |
| --- | --- | --- | --- | --- | --- | --- |
| chromatography | | | | | | |

EXAMPLE 2

The propagated cells (18 kg) of *Proteus mirabilis* produced as in Example 1 were suspended in a 2.8% perchloric acid aqueous solution (54 l.) and sonicated with Kubota Model 200µ sonic generator at 180 W for 7 minutes. Then, to the suspension was added a 2.8% perchloric acid aqueous solution in twice the volume of the suspension. The mixture was centrifuged at 8,500 G for 20 minutes and the supernatant was stirred for 30 minutes after addition of activated charcoal while stirring in a proportion corresponding to 5 g/l. and then filtrated. The activated charcoal was charged in a column, washed with 18 l. of 0.1 N hydrochloric acid and then with 18 l. of 10% aqueous ethanol, and eluted with 18 l. of 30% aqueous ethanol to give 30% aqueous ethanol fractions which combined and concentrated at 37° C. under reduced pressure.

The concentrate (30 ml) was separately fractionated as 15 portions of 2 ml. each by passing through a column (1.5 cm in diameter × 60 cm long) filled with Sephadex LH-20 (manufactured by Pharmacia Fine Chemicals AB, Sweden). In each fractionation operation, the eluate was collected as fractions of 3.2 ml each. Since the active substance was eluted in fractions No. 22–57 of each operation, then they were combined and evaporated at 37° C. under reduced pressure. The concentrate was charged in a column (10 cm in diameter × 30 cm long) filled with Polystyrene gel G 3000 S (manufactured by Toyo Soda Kabushiki Kaisha, Japan) and eluted with distilled water and then 10% aqueous ethanol. Since the active substance was present in both water fractions and 10% aqueous ethanol fractions, each of the fractions was separately concentrated and subjected to the following operations.

With respect to the water fractions, acetonitrile was added dropwise to the concentrate to give a white precipitate which was collected by centrifugation at 3,000 r.p.m.

On the other hand, for the 10% aqueous ethanol fractions, the concentrate was chromatographed with Toyo Filter paper No. 526 using acetic acid-n-butanol-water (3:12:5; v/v) as a developing solvent by ascending method, and the resulting spot at an Rf of 0.16 was extracted with water and concentrated to give the purified object substance.

Experiment 1

Wister-Imamichi strain male rats weighing 120–140 g were adrenalectomized and glutted with CE-2 type of solid food (manufactured by Clea Japan Inc., Japan) and with physiologically saline solution as water supply for 5–7 days. The rats were divided into groups of 4 members each and the members of each group were intraperitoneally administered with dexamethasone alone in a dose of 0.2–100 µg/100 g body weight or dexamethasone (0.2–100 µg/100 g) plus GSF (0.25 µg/100 g). Nine hours after the administration, the rats were sacrificed and the activities of tyrosine transaminase in their livers were determined.

The determination of the activities was carried out in the same ways by Roson et al., reported in J.B.C 238, 3725-3729, (1963), and the amount of enzyme corresponding to the amount such that 1µ mole of p-hydroxyphenylpyruvic acid is formed per minute was defined as one unit. The determined values are shown in FIG. 2.

As is clearly shown in FIG. 2, the administration of 1 µg of dexamethasone only indicated activities of tyrosine transaminase comparable to those obtained in case no reagent was administered. (Curve I) In contrast, when GSF (0.25 µg/100 g body weight) was administered in addition to dexamethasone (1 µg/100 g body weight), the enzyme induction was extremely amplified to a level which corresponds to that of the administration of about 5 µg of dexamethasone alone. (Curve II)

Incidentally, the administration of GSF alone did not affect the enzyme induction.

Experiment 2

L 5178 Y Lymphoblast in the number of $3.84 \times 10^6$ cells/head were implanted in the inguinal region of DAB/2 strain mice weighing 13-15 g which had been divided into groups of 3 mice each. Two days after the implantation, the mice were intraperitoneally administered with triamcinolone alone or triamcinolone plus GSF at 4 times every two days, and the inhibitory action on the growth of the lymphoblast cells was observed. Ten days after the implantation, mice were sacrificed and their tumors were weighed. The results are shown in the following Table 2.

Incidentally, the concentrated solution which was produced as fractions No. 22-57 from column with the Sephadex LH-20 as in Example 2 and concentrated to 300 ml. was used, as the test GSF.

TABLE 2

| dose of triamcinolone (mg/Kg body weight) | tumor weight* (g) | |
|---|---|---|
| | triamcinolone alone | triamcinolone + GSF (1 ml/Kg body weight) |
| 0 | 0.781 | 0.276 |
| 0.5 | 0.875 | 0.441 |
| 1.0 | 0.486 | 0.395 |
| 4.0 | 0.230 | 0.307 |
| 15.0 | 0.148 | 0.250 |

*Tumor weight is an average of three mice.

As is clear from Table 2, in the groups of mice administered with triamcinolone plus GSF, an approximately constant inhibitory action the growth of the lymphoblast was observed independently of the amount of triamcinolone administered. Especially, GSF indicated the inhibitory action on the growth of the lymphoblast even in case no triamcinolone was administered. Therefore, it is believed that the administration of GSF can amplify not only the action of glucocorticoid administered with GSF but also the action of those originally present in a living body.

Experiment 3

L 5178 Y Lymphoblast in the number of $4.5 \times 10^6$ cells/head were implanted in the inguinal region of DAB/2 mice weighing about 15 g which had been divided into groups of 5 mice each. Two days after the implantation, the mice were intraperitoneally administered with GSF which was the same as that used in Experiment 2 in different dose such as 0.05, 0.2, 0.4, 0.8 or 1.5 ml./kg body weight at 4 times every two days, and observed the inhibitory action on the growth of the lymphoblast cells. Ten days after the implantation, the mice were sacrificed and their tumor were weighed.

The results are shown in the following Table 3.

TABLE 3

| dose of GSF (ml/kg body weight) | tumor weight (g) (mean ± standard deviation) |
|---|---|
| 0 | 2.12 ± 0.37 |
| 0.05 | 2.10 ± 0.57 |
| 0.2 | 1.75 ± 0.22 |
| 0.4 | 1.36 ± 0.38* |
| 0.8 | 1.51 ± 0.22* |
| 1.5 | 1.45 ± 0.20** |

*P <0.05
**P <0.01

What is claimed is:

1. A glucocorticoid sparing factor characterized in that:
   it is a colorless and acidic substance produced in a culture broth of a microorganism of the Family Enterobacteriaceae and is easily soluble in water and in diluted aqueous acid or alkali;
   it is positive to 1,10-phenanthroline reaction, Orcinol reaction and Anthrone reaction and negative to Folin-Thiocalt reaction and Elson-Morgan reaction;
   it has a molecular weight between about 800 and about 1,500;
   it is an oligosaccharide having N-acetylneuraminic acid, pentose, hexose and a primary amine as constructing moieties;
   it indicates in vivo an amplifying action in the induction if tyrosine transaminase and leucine transaminase by glucocorticoid in the liver of adrenalectomized rat, with said amplifying action being deactivated by the action of α-glucosidase, but not being affected by the action of α-amylase, neuraminidase, hyaluronidase, lysozyme, chymotripsin, trypsin, pepsin, proteinase, papain, collagenase, aminopeptidase M, carboxypeptidases A and B, leucine-aminopeptidase, deoxyribonuclease 1, ribonuclease $T_1 + A$, acid phosphatase or alkali phosphatase;
   it does not influence induction of liver tyrosine transaminase in adrenalectomized rat when administered alone nor does it influence such induction by glycagon or insulin;
   it indicates an amplifying action on the induction of tyrosine transaminase by glycocorticoid in an in vitro system using the liver of an adrenalectomized rat under the perfusion method when added to the system prior to or at the same time as the administration of glucocorticoid;
   it is stable for more than 6 months at −20° C;
   it is stable for minimum 48 hours in a buffer solution having a pH of 4.2-9 at 37° C.;
   it is deactivated to form reducing sugar when heated at 105° C. for 12 hours in 6N hydrochloric acid;
   it has shoulder at 265 nm in untraviolet absorption spectrum and, after purification in a proper manner, a sharp peak appears at the same wavelength; and
   it has an Rf of about 0.16 as measured by ascending method using filter paper and acetic acid-n-butanol-water (3:12:5, v/v) as a developing agent.

2. A process for the production of the glucocorticoid sparing factor according to claim 1 which comprises cultivating a microorganism of the Family Enterobacteriaceae and isolating said factor from the culture broth.

3. A process for the production of the glucocorticoid sparing factor according to claim 1 which comprises cultivating a microorganism of the Family Enterobacteriaceae, extracting the bacterial substance from the propagated cells by destructing said cells, deproteinizing the extract, causing the extract to be adsorbed on activated charcoal, eluting the adsorbate with an organic solvent-containing solution, and purifying the eluate with gel filtration or column chromatography on ion exchange resin.

4. A process in accordance with claim 3 wherein said organic solvent-containing solution is selected from the group consisting of 0.2 N aqueous potassium hydroxide-acetone (3:7, v/v) and 10–30% aqueous ethanol.

5. A process in accordance with claim 3 wherein said gel filtration is effected with the use of a filter medium selected from the group consisting of those under the trade names of Sephadex G, Sephadex LH-20 and Polystyrene gel G 3000S.

6. A process in accordance with claim 3 wherein said ion exchange resin for the column chromatography is selected from the group consisting of DEAE cellulose and those under the trade name of Dowex 50 W.

7. A process in accordance with claim 3 wherein said microorganism of the Family Enterbacteriaceae is selected from the group consisting of those belonging to the general Escherichia, Aerobacter, Klebsiella, Paracolobactrum, Alginobactor, Erwinia, Serratia, Salmonella, Proteus and Shigella.

8. A process in accordance with claim 3 wherein said microorganism of the Family Enterobacteriaceae is selected from the group consisting of *Escherichia coli, Erwinia aroideae, Erwinia carotovora, Serratia marcesens, Proteus mirabilis, Proteus vulgaris, Proteus morganii* and *Aerobactor aerogenes.*

* * * * *